United States Patent [19]

Wild

[11] 4,095,458
[45] Jun. 20, 1978

[54] HYGROSTAT
[75] Inventor: Ernst Wild, Uerikon, Switzerland
[73] Assignee: Elektrowatt AG, Zurich, Switzerland
[21] Appl. No.: 777,409
[22] Filed: Mar. 14, 1977
[30] Foreign Application Priority Data
  Mar. 25, 1976  Switzerland .................. 3723/76
[51] Int. Cl.² ............. G01N 19/10; H01H 35/42; A01G 25/02
[52] U.S. Cl. ............................ 73/73; 61/13; 137/78; 200/61.06; 239/63
[58] Field of Search .............. 73/73, 337; 61/13; 137/78; 236/44 A; 239/63; 200/61.06

[56] References Cited
U.S. PATENT DOCUMENTS

| 1,773,086 | 8/1930 | Bahnson | 73/337 |
| 2,235,721 | 3/1941 | Morgan | 236/44 A |
| 2,743,552 | 5/1956 | Hunter | 137/78 |
| 3,204,872 | 9/1965 | Wear | 73/337 |

Primary Examiner—S. Clement Swisher
Attorney, Agent, or Firm—Werner W. Kleeman

[57] ABSTRACT

A hygrometer or hygrostat containing a hygroscopic body formed of wood.

6 Claims, 4 Drawing Figures

HYGROSTAT

BACKGROUND OF THE INVENTION

The present invention relates to a new and improved construction of a hygrometer or hygrostat.

Especially determinative of the response characteristic of hygrometers is the material from which its hygroscopic body is formed.

There are known to the art hygrometers whose hygroscopic body is formed of a hydrophilic plastic, especially a polyamide. With increasing ambient moisture this hygroscopic body lengthens or swells and with decreasing ambient moisture contracts or shortens. The selection of different polyamides, which possess these properties which are desirable for hygrometers, is comparatively limited.

The requirements placed upon hygrometers, namely, when such are employed for controlling watering or irrigation installations, are therefore so multifarious — due to the requirements to be fulfilled — that the existing selection of suitable plastics is not adequate in order to satisfactorily fulfill such requirements. With the heretofore known hygrometers there always is present a compromise between the properties offered by the plastics and the requirements placed upon the hygrometers.

For instance, the hygrometer firstly must be capable of responding with a considerable time-delay, even when the numerical value of the ambient moisture has reached the response value. Also, the hygrometer is confronted with the requirement that its response characteristic should not change linearly with the moisture content and/or the temperature of the surroundings, or that its response characteristic should possess hysteresis as a function of the time and/or as a function of the moisture content. With the prior art hygrometers it is therefore not possible to fulfill all of these requirements without resorting to the use of special regulation measures.

SUMMARY OF THE INVENTION

Therefore, with the foregoing in mind it is a primary object of the present invention to provide a new and improved construction of hygrometer which is not associated with the previously discussed drawbacks and limitations of the prior art proposals.

Yet another specific and important object of this invention aims at providing a hygrometer whose hygroscopic body is formed of a material, available in such a wide selection of types, that merely by virtue thereof it is possible to optimumly satisfy the individual requirements placed upon hygrometers without having to resort to the use of additional technical measures or expenditures.

Now in order to implement these and still further objects of the invention, which will become more readily apparent as the description proceeds, the proposed hygrometer of the present invention, is manifested by the features that its hygroscopic body is formed of wood.

The behaviour of the different woods with respect to adsorption- and desorption- capacity of water as a function of time, the temperature and/or the moisture content of the surroundings or ambient atmosphere and the thereby resultant volume changes are extensively known, so that one skilled in the art would experience no difficulty in selecting, for a specific field of application or use, the type of wood which is most suitable for this specific purpose. Furthermore, the degree of the elongation or contraction of the wood, which is dependent upon the moisture content thereof, also depends upon the direction in which the dimension change is measured in relation to the run of the grain or fibers.

BRIEF DESCRIPTION OF THE DRAWINGS

The invention will be better understood and objects other than those set forth above, will become apparent when consideration is given to the following detailed description thereof. Such description makes reference to the annexed drawings wherein.

DETAILED DESCRIPTION OF THE PREFERRED EMBODIMENTS

Figure 1A:
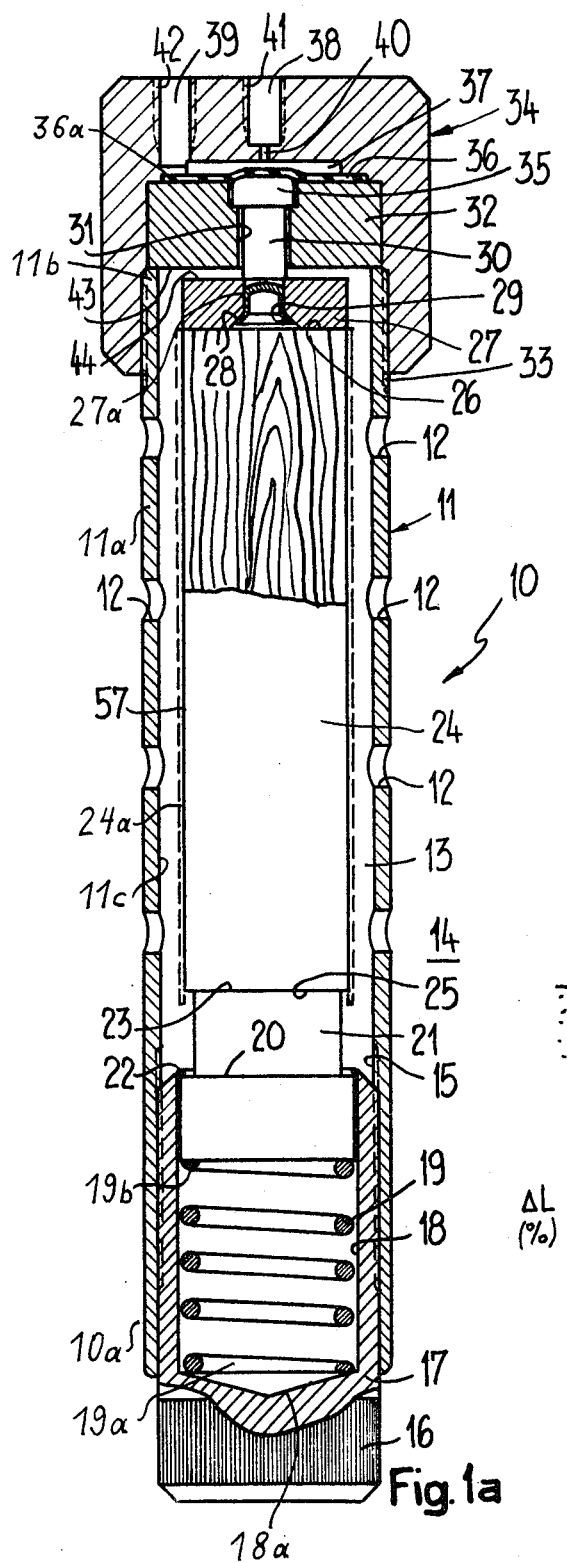
FIG. 1a is a longitudinal sectional view of a hygrometer i.e. a hygrostat constructed according to the invention and equipped with a membrane valve.

Describing now the drawings the hygrostat or hygrometer 10 illustrated by way of example, in FIG. 1 in longitudinal sectional view will be seen to comprise a tubular housing 11, for instance formed of stainless steel. Housing 11 includes a housing wall 11a equipped with a number of continuous holes or openings 12, for instance configured as open-ended bores or slots. The internal space or compartment 13 of the housing 11 thus freely communicates with the surrounding outer space or atmosphere 14. The one end 10a of the hygrometer 10 located at the lower portion of FIG. 1, is provided with internal threading 15, preferably fine threading. Screwed into this threading 15 is a plug 17 having a knurled portion or knob 16. Plug 17 includes a blind hole bore 18, at the base or floor 18a of which there bears one end 19a of a pressure or compression spring 19 or equivalent structure. The other end 19b of this pressure spring 19, which provides a compensation spring, bears against a plunger 21 provided at its outer circumference with a stepped portion or shoulder 20. Plunger 21 can be formed, for instance, of a hydrophobic plastic. The upper edge 22 of the plug or support 17 is flanged about the shoulder 20 of the plunger 21, so that the plunger 21 cannot unintentionally move out of the plug or support 17. At the free end surface or face 23 of the plunger 21 there is supported one base surface 25 of a substantially cylindrical or prismatic wooden rod 24. Wooden rod 24 is cut such that the run of the fibers or grains of the wood extends approximately parallel to the lengthwise axis of the wooden rod 24. It should be understood, however, that the wooden rod 24 also could be cut such that the run of the grain is transverse to the lengthwise axis of the rod 24. A disc or plate 27 is supported at the other base surface or end 26 of the wooden rod 24. This disc 27 is provided with a bore 27a having a countersunk portion 28. The bored-out end 29 of an actuation plunger 30 is riveted, by widening or upsetting such end 29, in the countersunk portion 28 of the bore 27a.

The actuation plunger 30 includes a head or head portion 35 which extends through a bore 31 of a closure block 32. This closure block 32 is fixedly clamped, in turn, by means of a cap screw or retaining nut 34 threaded onto external threading 33 provided at the upper end 11b of the housing 11.

The cap screw or retaining nut 34, in turn, sealingly clamps the marginal or peripheral edge 36a of a membrane or diaphragm 36 at the closure block 32. This membrane 36 is spanned over the head 35 of the actuation plunger or element 30. The cap screw or retaining nut 34 additionally possesses a machined or otherwise suitably formed portion which provides a valve chamber 37. An inlet 38 provided at the retaining nut 34 and equipped with threading 41 for fixing thereto a nipple or the like, flow communicates by means of a throttle location or throttle 40 with the valve chamber 37. The inlet 38 is arranged substantially coaxially with respect to the actuation plunger 30. On the other hand, there also extends from the valve chamber 37 an outlet 39 which is likewise provided with internal threading 42 for the attachment of a further nipple or the like.

From the foregoing description it will be apparent that with the described hygrostat or hygrometer 10 the switching element is formed by a membrane valve, the inlet 38 of which is closed upon elongation of the wooden rod 24 through the action of the actuation plunger 30 and the valve membrane 36, such elongation of the wooden rod 24 occuring in the presence of increasing moisture content.

The stroke of the actuation plunger 30 is limited, on the one hand, by the end surface 43 of the closure block 32 which confronts the housing 11 and, on the other hand, by the end surface 44 of the disc 27 which faces away from the wooden rod 24. This arrangement is accomplished in order to avoid that in the presence of extreme lengthening or elongation of the wooden rod 24 the membrane 36 will become unduly squeezed or crushed at the throttle location or throttle 40. If such extreme elongation or lengthening of the wooden rod 24 occurs, then this is taken-up by the pressure or compression spring 19 and the force which is thus produced by this pressure spring is then taken-up by the end surfaces 43, 44. The aforementioned membrane valve now can be beneficially employed, for instance, for directly controlling the infeed of water to the external space or room 14, as soon as such is needed, following the desired time-delay. On the other hand, the membrane valve also can be connected to operate as a pneumatic or hydraulic relay contact, which, in turn, controls a valve possessing a large throughflow rate or capacity, and the last-mentioned valve controls the infeed of water to the external space 14.

It is to be observed that, apart from the selection of the type of wood used for the rod 24, which advantageously is adhesively bonded to the plunger 21, there is afforded a further adjustment possibility by threading the plug 17 to a more or less greater extent into the housing 11. In this way the response threshold of the hygrometer 10 can be adjusted.

Figure 1B:
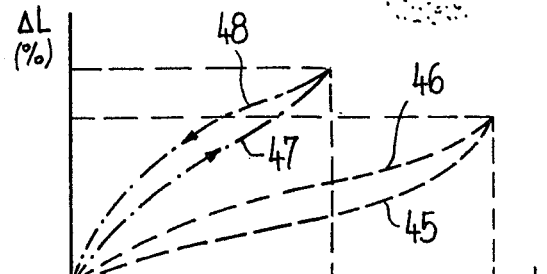
FIG. 1b is a diagram showing curves portraying the changes in length of two different types of wood as a function of time during the absorption and desorption of moisture through the wood.

Now in FIG. 1b there have been plotted as a function of the time t the length changes ΔL (in percent) during the adsorption (lengthening) and desorption (shortening) of two different types of wood. The broken line curve incorporating both of the branches 45 and 46 is characteristic of a hardwood, whereas the chain-dot line curve containing both of the branches 47 and 48 is characteristic, for instance, of a pine wood. Both curves show a clear hysteresis, and the curved branches 45, 47 in each case denote the adsorption phenomenon and the curved branches 46, 48 the desorption phenomenon.

From the curves of FIG. 1b it is possible to conclude, for instance, that for a given lengthening or elongation of a rod formed of hardwood there is required a much longer period of time than for a soft pine wood.

Figure 2:
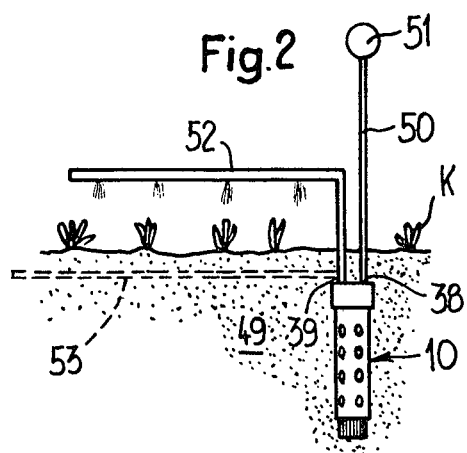
FIG. 2 illustrates one preferred field of application of the hygrometer of the present invention.

Now in FIG. 2 there is schematically illustrated by way of example, a field of possible use of the described hygrometer 10. This hygrometer 10 is embedded in the ground or nutrient medium 49 where there is cultivated the plants K or the like, hereinafter sometimes conveniently referred to simply as the "culture". The inlet 38 of the hygrometer 10 is connected by means of a connection line or conduit 50 with a main water line 51 which is under pressure. The outlet 39 of the hygrometer 10 is connected with an irrigation or watering line or conduit 52 which directly sprays the plants K, or with a seepage pipe or conduit 53 which is either located upon the ground or embedded therein and shown in broken lines in FIG. 2.

Figure 3:
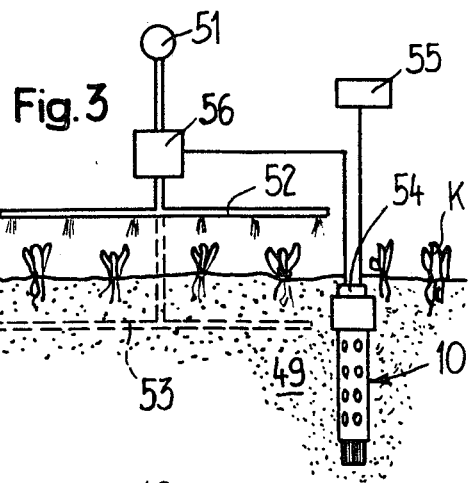
FIG. 3 illustrates another preferred field of use of the inventive hygrometer.

In the presence of large water requirements the hygrometer 10, as already explained, advantageously is to be connected as a relay, and such relay can be a fluidics- or electrical relay. An example of the last-mentioned case has been illustrated in FIG. 3. Here the hygrometer 10 is equipped with an encapsulated microswitch 54, actuated by the plunger 30, and connected in series between a current source 55 and an electromagnetic valve 56. This valve 56 is connected between the main conduit 51 and the watering or irrigation conduit 52 and the possibly employed seepage pipe or conduit 53 and practically assumes the function of the membrane or diaphragm valve of the hygrometer 10 illustrated in FIG. 2, but with a practically unlimited throughflow capacity.

With certain types of wood it is possible for there to be present in the wooden rod 24 itself a locally limited anisotrophy of the adsorption properties for moisture and therefore the elongation, so that the wooden rod apart from elongating, also curves. In order to extensively avoid this behaviour, the wooden rod 24 can be provided with a layer 57, as best seen by referring to FIG. 1, formed of a hydrophilic moisture pervious layer, for instance consisting of an open-pore foam. This layer 57 can be selected to be so thick that it practically fills the intermediate space between the jacket or outer surface 24a of the wooden rod 24 and the inner wall 11c of the housing 11.

While there are shown and described present preferred embodiments of the invention, it is to be distinctly understood that the invention is not limited thereto, but may be otherwise variously embodied and practiced within the scope of the following claims.

What I claim is:

1. A hygrostat comprising:
a hygroscopic body;
said hygroscopic body being formed of wood;
a pervious housing formed of hydrophobic material;
said hygroscopic body being arranged in said housing;
said hygroscopic body comprising a wooden rod having opposed ends;
means coupled with one end of said wooden rod;
a support element coupled with the housing for supporting the other end of said wooden rod;
stop means for limiting the stroke of said one end of said wooden rod;
a compensation spring operatively connected with said housing by means of said support element for coupling the other end of said wooden rod with said housing; and said support means is provided with means for adjusting the position of said compensation spring.

2. The hygrostat as defined in claim 1, wherein:
said means coupled with said one end of said wooden rod comprises a closure portion of a valve.

3. The hygrostat as defined in claim 1, wherein:
said means coupled with said one end of said wooden rod comprises a switch.

4. The hygrostat as defined in claim 1, wherein: said housing comprises a substantially tubular-shaped member equipped with openings;

and said support element including a threaded sleeve threadably secured into one end of the housing;

said compensation spring being arranged in said threaded sleeve.

5. The hygrostat as defined in claim 2, wherein:
said means coupled with one end of said wooden rod comprises a closure portion of a valve;

said valve constituting a membrane valve having a membrane; and a plunger supported at said one end of said wooden rod for actuating said membrane.

6. A hygrostat comprising:
a hygroscopic body;
said hygroscopic body being formed of wood;
a pervious housing formed of hydrophobic material;
said hygroscopic body being arranged in said housing;
said hygroscopic body comprising a wooden rod having opposed ends;
means coupled with one end of said wooden rod;
a support element coupled with the housing for supporting the other end of said wooden rod;
said means coupled with one end of said wooden rod comprises a closure portion of a valve;
said valve constituting a membrane valve having a membrane;
a plunger supported at said one end of said wooden rod for actuating said membrane;
said housing comprises a substantially tubular-shaped element provided with openings;
said support element including a threaded sleeve threaded into one end of said housing;
said compensation spring being arranged in said threaded sleeve;
said valve including a valve chamber;
a retaining nut threaded onto said housing;
said retaining nut being provided with said valve chamber;
said housing having an internal compartment; and
said membrane having peripheral edge means which seal said valve chamber with respect to said internal compartment of said housing.

* * * * *